US00PP17727P2

(12) United States Plant Patent
Tallman

(10) Patent No.: US PP17,727 P2
(45) Date of Patent: May 15, 2007

(54) BLACK RASPBERRY PLANT NAMED 'EXPLORER'

(50) Latin Name: *Rubus occidentalis*
Varietal Denomination: Explorer

(76) Inventor: Peter H. Tallman, 5690 Steeplechase Dr., Longmont, CO (US) 80503

( * ) Notice: Subject to any disclaimer, the term of this patent is extended or adjusted under 35 U.S.C. 154(b) by 36 days.

(21) Appl. No.: 11/116,993

(22) Filed: Apr. 27, 2005

(51) Int. Cl.
*A01H 5/00* (2006.01)

(52) U.S. Cl. ..... Plt./204
(58) Field of Classification Search ..... Plt./204
See application file for complete search history.

*Primary Examiner*—Kent Bell
*Assistant Examiner*—June Hwu
(74) *Attorney, Agent, or Firm*—Stratton Ballew PLLC

(57) ABSTRACT

A new and distinct primocane-fruiting (autumn-bearing) cultivar of black raspberry, *Rubus occidentalis,* named 'Explorer.' The 'Explorer' black raspberry was created as an $F_2$ generation seedling of a controlled cross between two unnamed black raspberry plants collected from uncultivated areas. 'Explorer' black raspberry is capable of providing a reliable and productive crop of large black raspberries on primocanes in late summer and early autumn when there are no fresh black raspberries available from other cultivars of black raspberry. The canes of 'Explorer' black raspberry also exhibit fewer thorns than canes of a typical black raspberry plant.

5 Drawing Sheets

Genus and species: *Rubus occidentalis.*
Variety denomination: 'Explorer'.

DESCRIPTION OF RELATED PRIOR ART

Several primocane-fruiting red raspberries are known commercially. Examples include red raspberry cultivars 'Heritage,' not patented, and 'Caroline,' described in U.S. Plant Pat. No. 10,412.

*The Small Fruits of New York,* by U. P. Hedrick, New York State Agriculture Experiment Station, Geneva, N.Y., 1925, lists about fifteen named varieties of primocane-fruiting black raspberry, the earliest named and most widely distributed of which was 'Ohio Everbearing.' As of 2004, there was no known source for 'Ohio Everbearing' or any other primocane-fruiting black raspberry variety. The same reference also includes one named variety of black raspberry which was described as thornless, and another named variety described as nearly thorn free. As of 2004, there was no known commercial source for partially or fully thornless black raspberries.

*Raspberries and Blackberries: Their Breeding, Diseases and Growth,* by D. L. Jennings, 1988, ISBN 0-12-384240-9, describes the existence of primocane-fruiting black raspberries in the past, including 'Ohio Everbearing,' but indicates that the primocane-fruiting trait is unusual for black raspberries.

In an effort to extend the harvest season, a grower will sometimes mow down floricanes of a summer-fruiting, non-primocane-fruiting black-raspberry cultivar in early spring, to about 20 cm high, forcing fruiting laterals to grow from the remaining lower portion of the cane. Berries growing on these laterals will begin ripening after ripening is complete in a typical floricane crop. While these fruiting laterals may appear to have some characteristics similar to fruiting primocanes, they are not very productive and they die at the end of the season, thus proving that they are not primocanes. Usually, the berries ripen on such fruiting laterals earlier than berries ripen on the primocane of a true primocane-fruiting black raspberry such as 'Explorer.'

BACKGROUND OF THE INVENTION

The 'Explorer' black raspberry is a product of a planned breeding program conducted by the inventor starting in Poughkeepsie, N.Y. and continuing in Longmont, Colo.

The 'Explorer' black raspberry originated from a controlled cross performed by the inventor between two selections from uncultivated areas, which will be referred to as W1 and W2 for purposes of this description. Selections W1 and W2 were neither named not patented.

The black raspberry plant described herein as W1 was a primocane-fruiting black raspberry plant discovered by the Inventor in the autumn of 1986 in an overgrown but previously landscaped residential area in Poughkeepsie, N.Y. and collected in the spring of 1988. W1 exhibited a reliable primocane-fruiting habit over the several years observed, but it had small berries and a small number of berries on each primocane, so it was not commercially useful.

The black raspberry plant described herein as W2 was the asexually propagated progeny of a black raspberry plant discovered in an uncultivated area near Rogers, Ark. and collected in the summer of 1991. W2 demonstrated an unusually large berry size for an uncultivated black raspberry. W2 did not exhibit the primocane-fruiting trait.

The controlled cross W1×W2 was made by the inventor using floricane flowers in the spring of 1993 in Poughkeepsie, N.Y. W1 was the seed parent and W2 was the pollen parent. The $F_1$ generation seedling from the W1×W2 controlled cross that is the parent of the instant invention was grown in Longmont, Colo. and selected in July 1999 for its large floricane-crop berries on a vigorous plant; it did not exhibit the primocane-fruiting trait. From open-pollinated seeds produced by this selected $F_1$ seedling, a population of $F_2$ generation seedlings of the cross W1×W2 was planted in a cultivated area in Longmont, Colo. in May 2001. The 'Explorer' black raspberry in the present invention was selected from this population of $F_2$ generation seedlings in August 2002, based on primocane fruiting with large and attractive berries, high number of fruits on each primocane, and vigorous growth. Some berries of the selection weighed over 2 grams at the time of selection. It was later discovered that the canes of the 'Explorer' black raspberry exhibit generally fewer and smaller thorns than canes of standard black raspberry cultivars.

During commercial evaluation trials, the 'Explorer' black raspberry was asexually propagated and tested as numbered selection PT9301.A.3.

The primary market for 'Explorer' black raspberry plants is expected to be home growers, U-pick growers, farmers-market growers, and specialty-food growers for production of fresh black raspberries in the late summer and early autumn season. There may also be a market for 'Explorer' black raspberry plants for use in certain unmechanized black raspberry production environments where the grower is seeking to reduce the effort and injury involved in managing the plot by reducing unwanted tip rooting and reducing the number of thorns encountered during pruning and harvesting.

ASEXUAL REPRODUCTION

Asexual reproduction of the 'Explorer' black raspberry was accomplished by rooting primocane cuttings in Longmont, Colo. by the Inventor in autumn 2003. After new canes sprouted from successfully rooted cuttings, additional asexual reproduction was accomplished during the following winter (2003–2004) by allowing the ends of some of these newly sprouted canes to tip root. An asexually propagated plant of 'Explorer' black raspberry planted in spring 2004 produced large primocane berries in autumn 2004. The ability to ripen berries on primocanes and the substantially identical berry weights and drupelet counts for this asexually propagated plant compared to the original selection demonstrate that the unique features of this new black raspberry are stable and reproduced true to type in the successive generation. The ability to bear fruit during the first year after being asexually propagated demonstrates that the primocane-fruiting habit is fully established and precocious in the asexually propagated plants. Further asexual reproduction of 'Explorer' using meristem tissue-culture methods was accomplished in South Deerfield, Mass. between 2004 and 2006.

SUMMARY OF THE NEW CULTIVAR

The following characteristics have been repeatedly observed and are determined to be the basic outstanding characteristics of 'Explorer' black raspberry as a new and distinct cultivar:

1. Reliable primocane-fruiting production of black raspberries every year, then floricane fruiting the following year on surviving floricanes that are retained.
2. Production of black raspberries that ripen in late summer and early autumn, after the normal season for floricane production of black raspberries and before an autumn freeze terminates production.
3. Large berry size, with primocane-produced berries usually exceeding a weight of 1.2 grams, and with some berries exceeding 2 grams each. A few berries up to 2.7 grams have been observed.
4. Large number of berries on a primocane, with healthy branched primocanes having more than 15 fruits on a single branch and sometimes up to 45 berries on a single branch. A combined count of over 50 flower buds, flowers, and berries on a single unbranched primocane was observed.
5. Generally fewer and smaller thorns on the upper portions of the primocane than would be expected on other available black raspberry cultivars.

COMPARISON TO EXISTING CULTIVARS

The 'Explorer' black raspberry can be compared to the black raspberry cultivar 'Bristol' (unpatented), which was released in 1934 by the New York Fruit Testing Association in Geneva, N.Y. Compared to 'Bristol,' the 'Explorer' black raspberry reliably produces fruits on primocanes, whereas 'Bristol' is not known to produce fruits on primocanes, only on floricanes. If floricanes of 'Bristol' do not survive the winter; there is no crop in the summer. Production of 'Explorer' black raspberry on primocanes may be accomplished in certain regions even after winter damage to the overwintered canes, provided the crown can be protected from winter injury.

The 'Explorer' black raspberry can be compared to the black raspberry cultivar 'Haut' (unpatented), which was developed at the University of Maryland and released in 1984. The 'Haut' black raspberry cultivar was not released as a primocane-fruiting cultivar and only occasionally develops flowers on primocanes. The inventor grew 'Haut' black raspberry for several years in Longmont, Colo. In only one of those years, 'Haut' black raspberry formed primocane flowers on one plant very late in the season and was unable to ripen fruit on primocanes before the primocanes were forced into dormancy by a hard freeze. The 'Explorer' black raspberry reliably produces fruit on primocanes every year and produces fruit early enough to ripen berries well before frost in most years as grown in Longmont, Colo.

Primocanes of summer-fruiting black raspberry cultivars, for example 'Cumberland' (unpatented) or 'Bristol,' arch over at mid-summer and continue growing downward rapidly in preparation for self-induced asexual propagation through tip-rooting by the end of the growing season. After the plant is mature, the 'Explorer' black raspberry plant seldom propagates itself by tip rooting. The 'Explorer' black raspberry has not been observed to spread by root suckering as is exhibited by many red raspberry cultivars. Thus, compared to many other black raspberry and red raspberry cultivars, the 'Explorer' black raspberry cultivar requires less effort by the grower to remove unwanted self-propagated plants from the established plots.

The 'Explorer' black raspberry has generally fewer and smaller thorns present on the upper portion of the canes compared to other black raspberry cultivars such as 'Jewel', 'Haut' and 'Bristol.' This reduces personnel injury from thorns during manual picking and pruning of the 'Explorer' black raspberry compared to manual picking and pruning of other cultivars.

DETAILED DESCRIPTION OF THE NEW VARIETY

Figure 1:
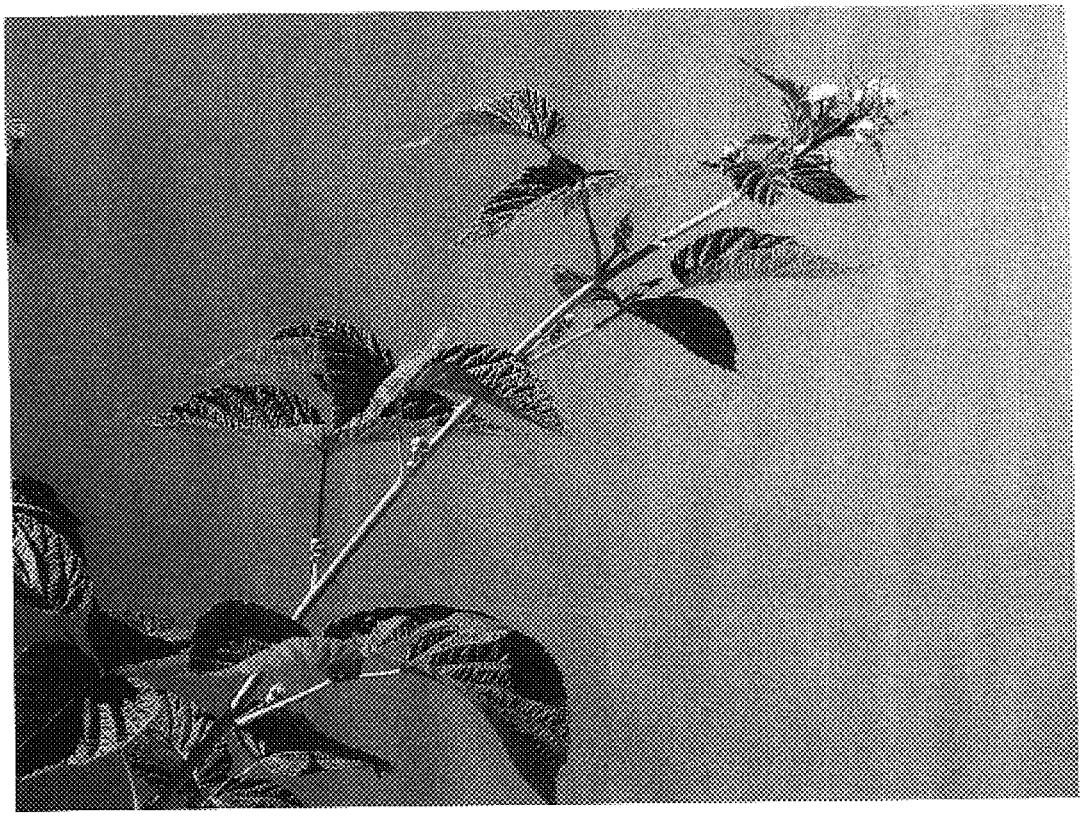
FIG. 1 illustrates the upper section of a primocane of 'Explorer' at the time the first primocane flowers are opening.

The 'Explorer' black raspberry has not been observed under all possible environmental conditions. The phenotype may vary somewhat with variations in environment such as temperature, humidity, day length, light intensity, water, nutritional status, and pruning practice without, however, any variance in genotype.

Some of the following description is based on observations made during the 2004 growing season from the originally selected 'Explorer' black raspberry plant in its fourth growing season in Longmont, Colo. This plant was grown in a garden bed prepared with native clay soil enhanced with compost mix and peat moss, along with treatment of superphosphate and soil sulphur applied according to label directions at the time of preparation. The plant was mulched with straw, grass clippings, and pine bark mulch, and fertilized lightly in spring 2004 with 10-10-10 fertilizer. The plant was fertilized again in early July and early August with a water-soluble acidifying fertilizer applied from a hose-end sprayer. The growing conditions in the spring of 2004 caused the floricane and primocane flowering and berry ripening dates to be about 10 to 14 days earlier than they would be in a more typical season. Additional data was taken during the 2006 growing season from the original plant and from asexually propagated progeny of the original plant propagated between 2003 and 2006 and growing in substantially the same conditions and soil.

The colors are described based on the plates of The Royal Horticultural Society Colour Chart, fourth edition, 2001.

All weights in gram units were measured to ±0.01 grams and then rounded to 0.1 gram units.

Primocane growth and appearance: A primocane of 'Explorer' black raspberry that emerges in the spring goes on to produce fruit in the same year. Once established, each plant normally produces several such primocanes from the same crown. In late June or early July, the primocane can be tip pruned to reduce arching and increase the number of fruits to be produced by the primocane. Alternatively, the primocane can be left unpruned, which allows the ripening of berries earlier than if the canes are pruned, although there will be fewer berries on the cane. After tip pruning, several branches are formed from each primocane. Two of the three primocanes of the observed plant were tip pruned on Jun. 13, 2004. The third of three primocanes was tip pruned on Jul. 8, 2004.

Primocane length and overall height and width of the plant depend on soil conditions, branching habit of the plant, pruning treatment, type of support, age of the plant, vigor of the plant, and competition for light with other plants or objects. As a result, these characteristics cannot be readily described as cultivar characteristics. The formation of flowers on the end of a primocane or primocane branch terminates further primocane extension at that site. Immature 'Explorer' plants have been observed to be less likely to form flowers than are more mature plants. Plants that have been asexually propagated using meristem tissue-culture are apparently rejuvenated by the tissue-culture process and, as a result, do not readily form flowers in the first growing season. Some supported primocanes of plants propagated by tissue culture were observed to growth in excess of 3 meters long in their first season in 2006. On more mature plants, after floricanes were removed during the dormant season, supported primocanes were observed to 2006 to branch spontaneously without tip pruning and had primocanes that were typically in the range of 1.1 meters long; such plants appeared to be approximately 1.1 meter high and 0.7 meters wide, although some primocanes on the same plants grew without termination to approximately 2 meters long in 2006.

An immature or weak 'Explorer' black raspberry plant will occasionally propagate itself by tip rooting instead of producing flowers on the end of the primocane, but this behavior is generally inhibited by formation of flowers once the plant is mature enough to start fruiting.

Primocanes:

*Habit.*—Semi-upright to arching.

*Quantity.*—On the original plant, three primocanes grew from the crown in 2004; the plant produced three, four, and five branches on the three primocanes.

*Color.*—Stem with waxy bloom — blue-green 122D (Jun. 28, 2004); base of cane with waxy bloom — violet-blue 95D; base of cane with waxy bloom rubbed off greyed-purple 183B (Sep. 4, 2004); branches with waxy bloom greyed-green 188D (Sep. 4, 2004); branch with waxy bloom rubbed off yellow-green 144B (Sep. 4, 2004).

*Diameter.*—0.9 cm to 1.2 cm at base of primocane.

Figure 2:
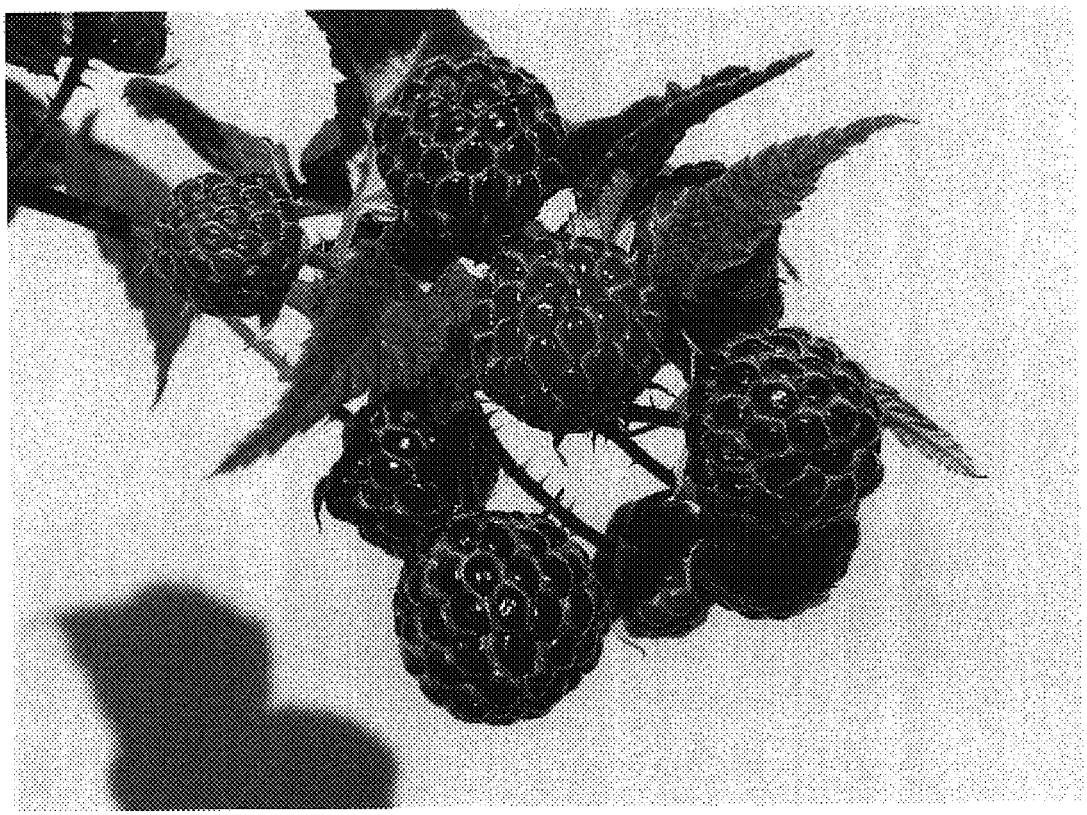
FIG. 2 illustrates detail of the black raspberries ripening at the end of a primocane of 'Explorer' as grown in Longmont, Colo. The photograph also illustrates the general thorniness surrounding the berry cluster.

*Thorns.*—Sharp. At base, average 41 thorns per 30 cm of cane, average length 0.43 cm; at midpoint, average 17 thorns per 30 cm of cane, thorn length average 0.29 cm; at end of branch of branched primocane, 4 thorns per 30 cm of cane, thorn length average 0.28 cm; thorns numerous around berry clusters, as shown in FIG. 2, average length 0.13 cm; usually 1 or 2 present on petiole of compound leaf, average length 0.17 cm; sometimes-1 or 2 present on underside of each leaflet or petiolule of compound leaf, each approximately 0.11 cm long. Thorn color from mid-point of mature primocane with waxy bloom rubbed off: exposed top side greyed-red 810B, bottom side greyed-yellow 161C, tip greyed orange N170C (Sep. 14, 2006). Thorn shape wider at the base attachment point to the cane, tapering to a sharp point, sides concave, thorn pointing straight out from cane or reflexed slightly black toward older cane growth; oval-shaped area of thorn attachment at mid-point of cane average 0.35 cm long (parallel to the cane growth) and 0.17 cm wide.

*Leaves.*—Odd-pinnately compound with three leaflets; leaflets predominantly elliptical to cordate, margins irregularly serrate to double serrate, tips acute to acuminate, and base rounded to cordate; not pubescent; upper surface yellow-green 147A, lower surface color greyed-green 190B; later in season lower surface color between greyed-green 198B and 198C; serrations on the leaves 0.1 cm to 0.25 cm long. For a mature compound leaf, average overall length 14 cm, average overall width 13.4 cm. Mature leaflet average length 7.0 cm, average width 4.4 cm.

*Petiole.*—Length 4.5 to 6.5 cm; late season color, upper surface greyed-orange 174B, underside yellow-green 145C (Sep. 28, 2004).

*Petiolule.*—Length 0 to 0.2 cm for side leaflets, 1.3 to 2.3 cm for end leaflet; late season color exposed top side from mature leaf color greyed orange 177A; color bottom side, away from sun color yellow-green 150D; immature leaf exposed top side color green group 138A, bottom side, away from sun color yellow-green group N144D (all colors Sep. 14, 2006).

*Flower.*—Flowers begin forming in early summer; average flower bud just before opening 0.56 cm diameter; in 2004, first primocane flower opened July 21, 38 days after tip pruning on June 13; primocane flowers tend to be held upwards above surrounding foliage; flower petal color white 155C, petal average width 0.26 cm, petal average length 0.40 cm long; sepal average width 0.35 cm, sepal average length 0.61 cm, sepal color yellow-green 145B; overall open flower calyx width average 1.55 cm. As observed in August 2006, a primocane flower appears fertile for one or two days after opening, then loses petals, and after another day loses stamens and stigmata; weather during this period of observation was consistently warm and dry.

*Reproductive organs.*—Stamens numerous, length variable 0.19 to 0.38 cm, filament color white 155B to 155C, anther color initially greyed yellow 160C, later maturing to greyed orange 166A. Styles numerous, average length 0.25 cm, pistil color yellow-green 145C, later maturing to greyed-orange 166A. Central ovary cluster dome shaped, typically 0.33 cm wide, 0.28 cm high, color green 143A.

*Pedicel.*—Average length 1.6 cm; color yellow-green N146B; slightly pubescent; thorny; average 15 thorns of length 0.12 to 0.15 cm each.

*Disease.*—No susceptibility or resistance observed as grown in Longmont, Colo.

*Pests.*—No significant pest susceptibility or resistance observed compared to other cultivars as grown in Longmont, Colo.

*Heat.*—Primocanes and ripening fruit observed to be tolerant of heating conditions for Longmont, Colo., which is designated as American Horticultural Society heat zones 6 and 7. During the flowering and berry ripening season, daytime temperatures exceeded 95 degrees Fahrenheit.

Figure 3:
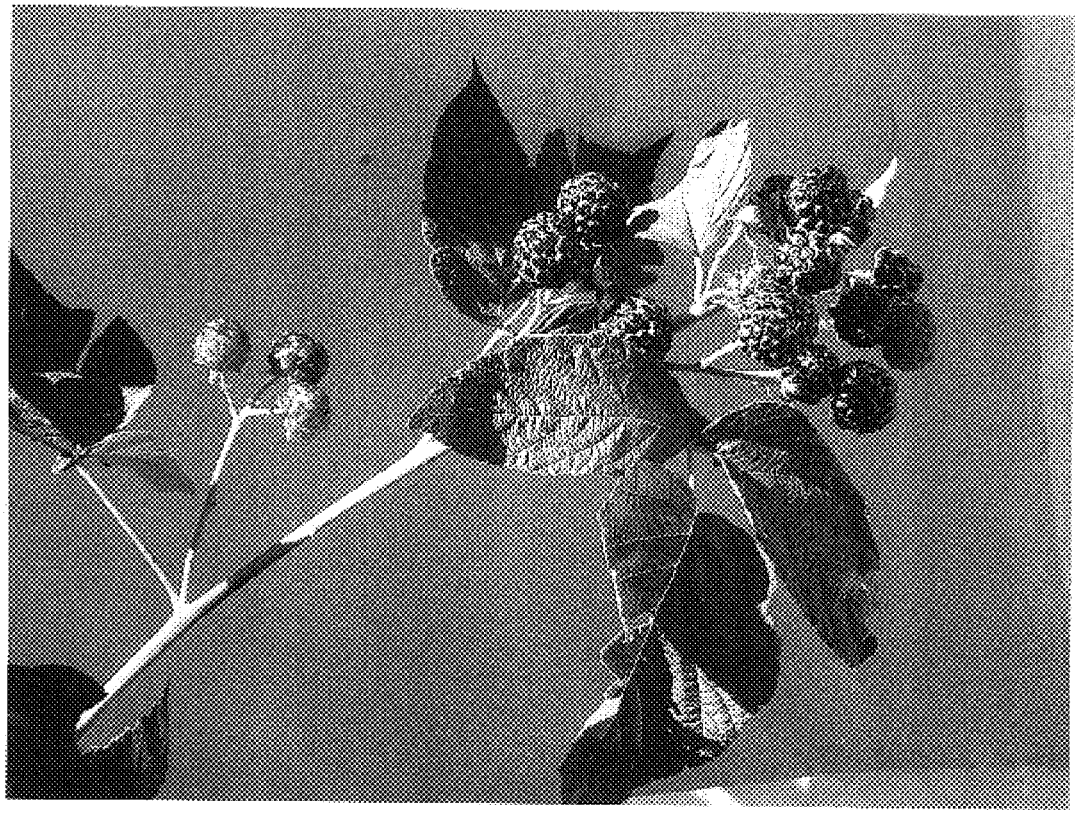
FIG. 3 illustrates the overall appearance of the end of one branch of a branched primocane of 'Explorer,' including ripe and unripe berries, primocane stem, and leaves. The small number of thorns on the upper primocane stem, exclusive of the leaves and berry clusters, is also shown.
Figure 4:
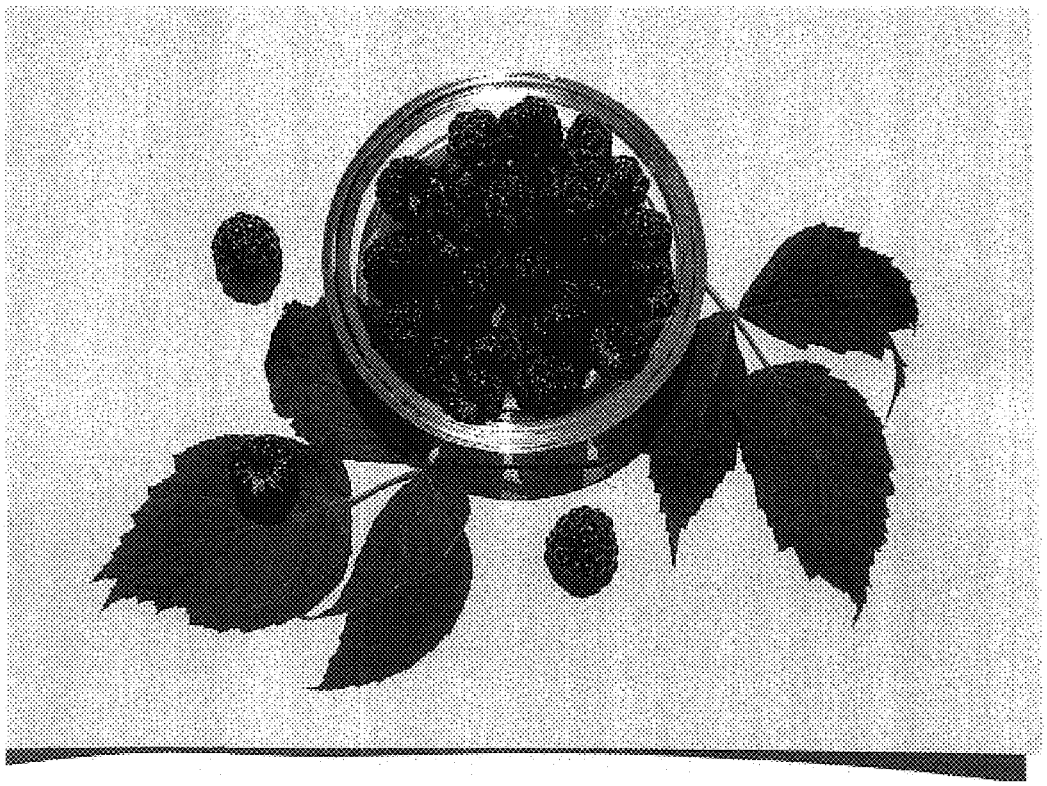
FIG. 4 illustrates one day's crop of berries harvested from a single 'Explorer' plant. Two compound leaves from a primocane of 'Explorer' are also shown. The outside diameter of the glass dish shown in the photograph is approximately 9.5 cm.
Figure 5:
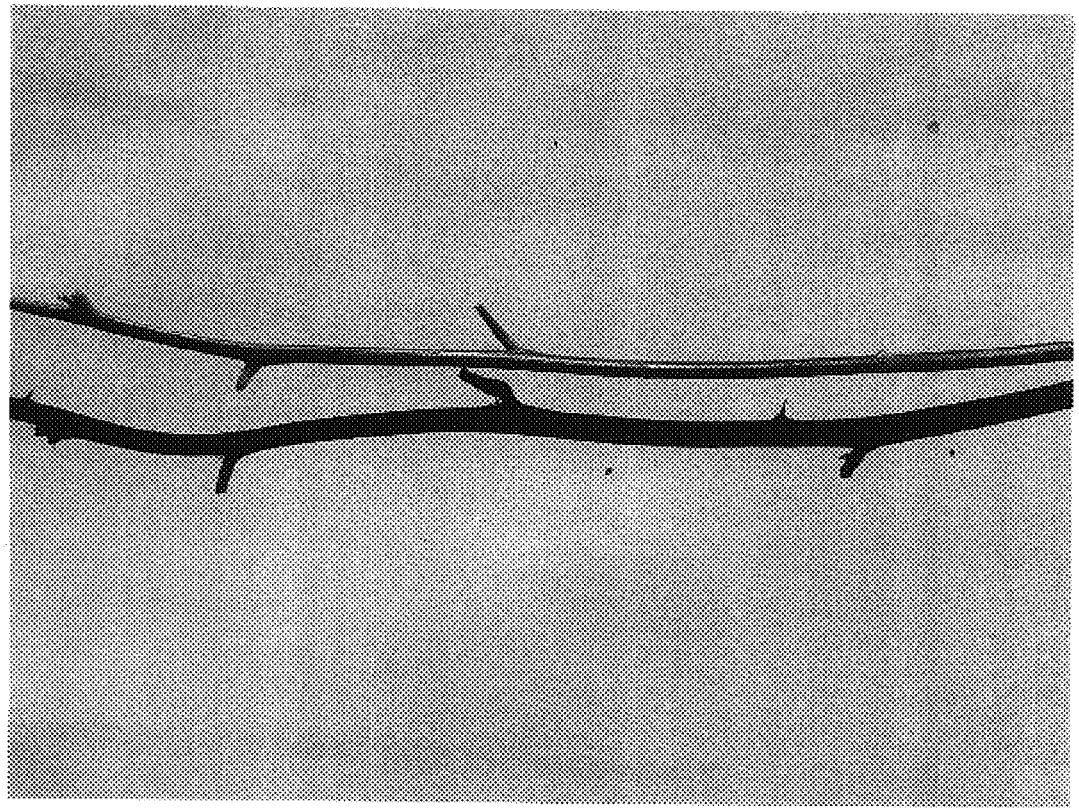
FIG. 5 illustrates a section of one branch of a branched primocane of 'Explorer' after the end of fruiting on the branch. Leaves were removed to illustrate the relatively low number of thorns on the upper portion of a primocane. Two thorns on this section can be identified by inspecting the silhouette shown in the shadow of the branch.

Ripening schedule of primocane berries: Timing of primocane berry ripening depends on floricane treatment, primocane tip pruning, plant age, and growing conditions. Eliminating floricanes before growth starts in the spring will cause primocane fruiting to be earlier than if floricanes are retained to fruit in the summer. Tip pruning to increase the berry count on a primocane will delay the start of ripening of berries on the primocane, with the particular ripening date somewhat dependent on the tip pruning date. On a single plant of several primocanes, several different ripening schedules can be induced by tip pruning different primocanes at different times. FIG. 3 shows the berries ripening on the end of a branch of a primocane on Sep. 8, 2004. Branching of the primocane had been forced by pruning the top of the primocane earlier in the season, which is standard horticultural practice for growing other cultivars of black raspberry and primocane-fruiting cultivars of red raspberry.

The first primocane fruits ripened on Aug. 28, 2004, which was 76 days after tip pruning on Jun. 13, 2004, and 38 days after the first flower opened on Jul. 21, 2004. The last berries on the primocane tip pruned on Jul. 8, 2004 ripened on Oct. 8, 2004, which was 91 days following tip pruning and 58 days following the start of flowering on this primocane. In 2006, on plants with floricanes removed while dormant, the first primocane fruits ripened on Aug. 11, 2006.

The ripening time for the berries can also be delayed somewhat by artificially holding a plant in dormancy past the normal time for primocane emergence in the spring; FIG. 2 illustrates the berries at the end of a primocane which started ripening berries on Oct. 23, 2004 from a plant given such delayed release from dormancy.

Primocane berries:

*Size.*—Large; earlier ripening berries tend to be larger than later ripening berries on the same primocane; average of measurements taken from first berries harvested, Aug. 28, 2004 — weight 2.0 g, diameter 17.8 mm, height 12.6 mm, 58 drupelets; average weight of berries harvested Sep. 8, 2004 — 1.5 g; average weight of all berries harvested in 2004 — 1.4 g.

*Color.*—Ripe berry, greyed-purple N186A to black 202A; slightly under-ripe berry, greyed-purple 187B; pulp of ripe berry (color of smear on white plate), red 45B.

*Shape.*—Overall near truncated sphere, usually truncated slightly below the equator, so slightly larger than a hemisphere; shape of several berries is illustrated in FIG. 2. Upon careful measurement, may be found toward truncated ellipsoid, also truncated slightly below the equator. Berry surface, as illustrated in FIG. 2, consists of the truncated-spherical exposed portions of many interlocked drupelets, some dimpled, each truncated above the equator; overall bumpy surface appearance usually associated with raspberries.

*Seeds.*—Average weight 2.1±0.1 mg.

*Flavor.*—Characteristic black raspberry flavor.

*Productivity.*—Total harvest 225 grams of primocane berries from the single observed plant in 2004.

*Acidity.*—pH 3.7 measured using a pH meter on pulp extracted from crushing ripe berries and straining to remove seeds.

*Sweetness.*—Soluble solids 10.2±0.2% as measured using a refractometer on juice extracted from ripe berries by freezing then thawing the berries.

*Receptacle.*—Receptacle left behind when the ripe berry is picked cylindrical to conical, rounded apex, average width 0.51 cm at the base, average length 0.69 cm, color yellow 8B to 8C; receptacle size and shape also describe the size and shape of the berry cavity.

*Hardiness.*—Ripening berries are frost tender.

*Heat.*—Tolerant of heating conditions for Longmont, Colo., which is designated as American Horticultural Society heat zones 6 and 7. Ripening berries observed to be tolerant of daytime temperatures of 95 degrees Fahrenheit or more before harvest.

Floricane and floricane fruiting: Much of the upper portion of the primocane that forms primocane flowers and berries in the autumn dies at the end of the growing season. The rest of the primocane goes dormant in late autumn then overwinters to become a floricane the next spring, when fruiting laterals form on the surviving portion. Flowers and berries form on the floricanes earlier in the growing season than on the primocanes. Berries ripen on floricanes through mid-summer. Following the end of floricane fruit ripening, the floricanes gradually decline and die.

Unless otherwise noted, floricane and floricane fruit and characteristics are not materially different from primocane and primocane fruit characteristics. Floricane berry productivity, acidity, and sweetness were not measured.

Floricanes:

*Cane color.*—Red-purple 59A and greyed-red 178A (December, dormant cane, waxy bloom rubbed off); greyed-purple 183B (early September, waxy bloom rubbed off). Laterals (Sep. 14, 2006) orange 26C.

*Length.*—Surviving overwintered portion, typical example, exclusive of fruiting laterals 80 cm. Fruiting laterals 16 cm to 33 cm, longer laterals initiated from nearer base of floricane.

*Hardiness.*—Hardy for Longmont, Colo., hardiness zone 5b (−15F. ° to −10F. ° average low temperature).

*Diameter.*—Portion surviving from primocane 1.1 cm at base, 1.0 cm at midpoint (early September); Base of new fruiting lateral 0.3 cm.

*Leaves.*—Size 13 cm long, 8.5 cm wide; leaflet size 4.2 to 5 cm long, 3.5 to 5 cm wide; petiole average length 3.6 cm; petiolule terminal leaflet average 1.3 cm, petiolule side leaflets 0 to 0.3 cm; leaflets not pubescent; color yellow-green 146A.

*Flower.*—First flower opened May 11, 2004.

Floricane berries:

*Size.*—Berries harvested Jun. 25, 2004 weighed an average of 1.3 g, with 50 to 60 drupelets; Berries harvested Jun. 27, 2004 weighted an average of 1.2 g; Berries harvested Jul. 5, 2004 weighed an average of 1.0 g.

*Seeds.*—Average weight 1.9±0.1 mg.

It is claimed:

1. I claim a new and distinct primocane-fruiting black raspberry plant substantially as described and illustrated herein.

* * * * *